United States Patent [19]

Bondi et al.

[11] Patent Number: 4,606,858

[45] Date of Patent: Aug. 19, 1986

[54] METHOD OF PURIFYING CAPROLACTAM

[75] Inventors: Enrico Bondi, Olmo; Paolo Senni, Colleferro, both of Italy

[73] Assignees: Snia BPD S.p.A.; Chimica del Friuli S.p.A., both of Italy

[21] Appl. No.: 699,520

[22] Filed: Feb. 7, 1985

[30] Foreign Application Priority Data

Feb. 8, 1984 [IT] Italy .......................... 19497 A/84

[51] Int. Cl.$^4$ ........................................... C07D 201/16
[52] U.S. Cl. .................................................. 540/540
[58] Field of Search ................................ 260/239.3 A

[56] References Cited

U.S. PATENT DOCUMENTS

| | | | |
|---|---|---|---|
| 2,221,369 | 11/1940 | Cass | 260/239.3 A |
| 3,145,198 | 8/1964 | Morbidelli et al. | 260/239.3 A |
| 4,239,682 | 12/1980 | Danziger et al. | 260/239.3 A |
| 4,301,073 | 11/1981 | Fuchs et al. | 260/239.3 A |

*Primary Examiner*—Robert T. Bond
*Attorney, Agent, or Firm*—Stiefel, Gross, Kurland & Pavane

[57] ABSTRACT

The invention is concerned with a method of purifying caprolactam as obtained by Beckmann transposition or by nitrosation of cyclohexyl compounds, characterized in that it comprises the following steps:

(a) the caprolactam oil is treated with ammonia to obtain a pH in the 8 to 10 range;

(b) the caprolactam in water-ammonia solution yielded by (a) is extracted with toluene;

(c$_1$) any caprolactam still in the toluene solution yielded by (b) is treated with NaOH;

(C$_2$) the aqueous phase left over from the extraction with toluene (b) is removed.

10 Claims, No Drawings

METHOD OF PURIFYING CAPROLACTAM

BACKGROUND OF THE INVENTION

1. Field of the Invention

This invention relates to an environmentally cleaner method of purifying caprolactam.

2. Prior Art

Known from the pertinent literature are methods of purifying caprolactam from:

(a) its solutions in $H_2SO_4$ following Beckmann transposition of cyclohexanoneoxyme, or (b) solutions in $H_2SO_4$ of the product resulting from nitrosation of cyclohexyl compounds and extraction of the unreacted cyclohexyl compound.

Such prior methods are characterized by the following process steps:

(1) neutralization of the sulphuric acid with $NH_3$ to form the so-called "oil of lactam", which stratifies over the saturated solution of ammonium sulphate;

(2) causticization of the lactam oil with NaOH (in order to salify impurities of an acidic nature);

(3) extraction with toluene (or another equivalent solvent) of the caprolactam from the caustic oil;

(4) a range of appropriate treatments, such as chemical treatments, re-extraction with water of the caprolactam from the toluene solutions, additional chemical treatments, and finally vaporizations and/or rectifications.

Step (2), namely causticization with NaOH, has two main disadvantages:

(a) disposal of the toluene-extracted caprolactam raffinate: this water-alkaline stream contains the sodium salts of the carboxylic acid impurities, the sodium salts of the organic carboxy-sulphonic impurities.

The only possible disposal technique is combustion of the whole stream; such combustion, however, is not devoid of some serious drawbacks, since the alkalis and chlorides present will corrode and attack the metal parts, as well as the refractories of the furnaces; further, during the combustion, there are formed meltable salts which, on the one side, tend to clog up the furnaces resulting in frequent stops, and on the other side, cause additional problems for their removal on account of their being present in large amounts (on the order of thousands of tons per year in the instance of a caprolactam plant having an 80,000 t/year capacity);

(b) poor solubility of the sodium salts of carboxysulphonic acids in causticized lactam oil, thereby causing precipitation of said salts in the extraction towers with toluene, which leads to frequent clogging, entrainments, poor separation of the phases, and accordingly, more or less long downtime for the plant.

The applicants have now unexpectedly found that such drawbacks can be fully obviated, where (1) the caprolactam oil is alkalized, rather than treated with NaOH, with ammonia to a pH in the 8 to 10 range;

(2) any caprolactam left in the toluene solution is treated with NaOH.

SUMMARY OF THE INVENTION

Accordingly, this invention is directed to a method of purifying caprolactam as obtained either by Beckmann transposition or by nitrosation of cyclohexyl compounds, characterized in that it comprises the following steps:

(a) the cparolactam oil is treated with ammonia to a pH in the 8 to 10 range;

(b) the caprolactam in water-ammonia solution yielded by (a) is extracted with toluene;

($c_1$) any caprolactam left in the toluene solution yielded by (b) is treated with NaOH;

($c_2$) the aqueous phase left over from the extraction with toluene according to (b) is removed.

DETAILED DESCRIPTION OF THE PREFERRED EMBODIMENTS

Treatment of the lactam oil with ammonia (step (a)) may be carried out with aqueous ammonia, or preferably, with gaseous ammonia, preferably up to a pH in the approximate range of 9 to 9.5. The treatment is carried out at a temperature below 65° C., preferably at room temperature for a time period varying preferably from 15 to 120 minutes. Extraction with toluene (as per step (b)) is carried out with conventional methods at a temperature in the 10° to 50° C. range, preferably in the 20° to 40° C. range, and more preferably at room temperature.

Treatment of caprolactam with NaOH (as per step ($c_1$)) may be carried out in accordance with the invention, such as (1) by treating the toluene extract with an aqueous solution of NaOH at a temperature below 45° C., preferably at room temperature.

The NaOH concentration selected for that treatment may vary preferably from 3% to 25%, more preferably from 5% to 15% by weight.

(2) Alternatively to (1) above, small amounts may be added (from 0.1% to 0.6% by the weight of the NaOH over caprolactam) during distillation of the caprolactam. The amount of NaOH over caprolactam is preferably in the by-weight range from 0.2% to 0.4%.

The addition of NaOH is expediently carried out following a first distillation under vacuum and in a thin film of the caprolactam so as to remove, as residue, the high-boiling impurities.

Of course, in accordance with the invention, both of the above treatments, ($c_1$) (1) and ($c_2$) (2), may be carried out similarly.

The caprolactam yielded by the method of this invention, which is also a part of this invention, is of the "fiber grade" type.

The following examples are illustrative and not limiting. Parts are understood to be by weight, unless specified otherwise. The caprolactam is designated C.L.

EXAMPLE 1

100 p/h caprolactam oil (containing 56.02 p/h caprolactam) as obtained with known methods following neutralization of the sulphuric acid with ammonia to a pH of about 3.5–3.8, is further treated with $NH_3$ to a pH of 9.4.

The resulting solution is extracted continuously in a rotary tray tower with 496.08 p/H toluene. 551.2 p/h of a solution overlying the 10% C.L. in toluene (hereinafter referred to as "toluene extract") and an underlying aqueous phase comprising 44 p/h of an aqueous ammonia solution containing essentially all of the byproducts and 0.897 p/h C.L. included with the starting lactam oil. The extraction yield is 98.4%.

EXAMPLE 1a 1,000 parts toluene solution of caprolactam (10% C.L.) is treated under powerful agitation at room temperature with 12 p aqueous solution of NaOH at 15%. Thereafter, the toluene solution of caprolactam is treated according to known methods as indicated. A caprolactam is obtained which has the following purity characteristics, volatile nitrogenous bases=0.35 meq/kg CL
N. of $KMnO_4$=9,000 sec.

EXAMPLE 1b 1,000 parts toluene solution of caprolactam (at 10% C.L.) is treated with NaOCL and $KMnO_4$ in accordance with known methods. The resulting anhydrous caprolactam (95 p) is distilled at least once under vacuum. The distilled caprolactam (78 p) is again distilled under vacuum in the presence of 0.2 p NaOH. After separating a first head fraction which is cycled back, 60 p caprolactam is yielded which has the following characteristics, volatile nitrogenous bases=0.2 meq/kg
N. of $KMnO_4$=10,600 sec.

EXAMPLE 1c

By operating as described in Examples 1a+1b, a "fiber grade" caprolactam is obtained which has the following characteristics:

volatile nitrogenous bases=0.2 meq/kg
N. of $KMnO_4$=12,200 sec.

We claim:

1. A method of purifying crude caprolactam obtained by (i) nitrosation of cyclohexyl compounds followed by (ii) contacting the crude material with sulfuric acid and then with ammonia to raise the pH to a range of about 3.5 to about 4.5, said method comprising the steps:
   (a) further contacting the crude caprolactam with ammonia to raise the pH to a range of about 8 to about 10, thereby yielding an aqueous composition containing caprolactam; and
   (b) contacting the aqueous composition containing caprolactam from step (a) with toluene to extract the caprolactam, thereby yielding a toluene composition containing caprolactam.

2. A method according to claim 1, wherein the treatment according to step (a) is carried out to a pH in the 9 to 9.5 range.

3. A method according to claim 1, wherein the treatment according to step (a) is carried out at a temperature in the range of from room temperature to 65° C.

4. A method according to claim 3, wherein said treatment is carried out over a time period of 15 to 120 minutes.

5. A method according to claim 1, wherein the extraction with toluene according to step (b) is carried out at a temperature in the range of from 10° C. to 50° C.

6. The method of claim 1 further comprising the step:
   (c) contacting a toluene composition containing caprolactam with an aqueous NaOH solution containing from about 3% to about 25% NaOH at a temperature less than about 45° C. and recovering purified caprolactam.

7. A method according to claim 6, wherein the treatment according to step ($c_1$) is carried out at room temperature.

8. A method according to claim 6, wherein the NaOH concentration in the acqueous solution varies between 5% and 15% by weight.

9. A method according to claim 6, wherein the treatment according to step ($c_1$) is carried out by adding an NaOH solution during distillation of the caprolactam in an amount equal to 0.1% to 0.6%, preferably to 0.2% to 0.4% by the weight of NaOH over the caprolactam.

10. A method according to claim 9, wherein the NaOH is added following a first distillation under vacuum and in a thin film of the caprolactam.

* * * * *